United States Patent
Büchler et al.

(10) Patent No.: US 6,286,371 B1
(45) Date of Patent: Sep. 11, 2001

(54) MONITOR HEAD FOR ULTRASOUND CONTROL BY PULSE ECHO PROCESS

(75) Inventors: Johannes Büchler, Siegburg; Manfred Rost, Wesseling; Torsten Niederdränk, Erftstadt, all of (DE)

(73) Assignee: Krautkramer GmbH & Co., Hurth (DE)

( * ) Notice: Subject to any disclaimer, the term of this patent is extended or adjusted under 35 U.S.C. 154(b) by 0 days.

(21) Appl. No.: 09/485,496
(22) PCT Filed: May 13, 1998
(86) PCT No.: PCT/DE98/01323
  § 371 Date: Feb. 10, 2000
  § 102(e) Date: Feb. 10, 2000
(87) PCT Pub. No.: WO99/08809
  PCT Pub. Date: Feb. 25, 1999

(30) Foreign Application Priority Data

Aug. 13, 1997 (DE) .............................................. 197 35 101

(51) Int. Cl.⁷ .............................. G01N 29/00; H01L 41/04
(52) U.S. Cl. .............................. 73/632; 310/311; 310/327
(58) Field of Search ................................. 73/514.34, 632, 73/649, 514.35; 310/313 A, 326, 327, 328, 331, 332, 334, 336, 364, 311, 321, 322

(56) References Cited

U.S. PATENT DOCUMENTS

| | | | |
|---|---|---|---|
| 4,446,739 | 5/1984 | Coursant . | |
| 4,649,313 | * 3/1987 | Ogawa et al. | 310/358 |
| 4,742,264 | * 5/1988 | Ogawa | 310/332 |
| 4,868,447 | * 9/1989 | Lee et al. | 310/328 |
| 5,233,256 | * 8/1993 | Hayashi et al. | 310/317 |
| 5,325,012 | * 6/1994 | Sato et al. | 310/364 |
| 5,578,845 | * 11/1996 | Masuda et al. | 257/295 |
| 5,629,906 | * 5/1997 | Sudol et al. | 367/162 |

FOREIGN PATENT DOCUMENTS

| | | |
|---|---|---|
| 34 41 563 | 5/1985 | (DE) . |
| 37 10 339 | 10/1988 | (DE) . |
| 2 083 695 | 3/1983 | (GB) . |

OTHER PUBLICATIONS

J. Buchler et al: "Electronic Circuit for High Frequency and Broad–Band Ultrasonic Pulse–Echo Operation" Ultrasonics, Mar. 1987, UK, Bd. 25, Nr. 2, Seiten 112–114, XP002081342, ISSN 0041–624X.

* cited by examiner

Primary Examiner—Richard A. Moller
(74) Attorney, Agent, or Firm—Akerman Senterfitt

(57) ABSTRACT

The invention concerns a monitor head for ultrasound control by pulse echo process, in particular for producing a brief ultrasound pulse, unipolar as far as possible, comprising an oscillator/transmitter (26) and an oscillator/receiver (32), each provided with electrodes (28, 30, 34, 36). The oscillator/transmitter (26) and the oscillator/receiver (32) are made of the same material. The oscillator/transmitter (26) and the oscillator/receiver (32) are arranged directly one behind the other, in the sound propagation direction, in particular flat-bonded one on the other.

16 Claims, 2 Drawing Sheets

MONITOR HEAD FOR ULTRASOUND CONTROL BY PULSE ECHO PROCESS

FIELD OF THE INVENTION

The invention relates to a probe for ultrasonic testing according to the pulse-echo method, in particular for generating a short, possibly unipolar ultrasound pulse, provided with a transmitter transducer and with a receiver transducer, each of them being provided with electrodes.

BACKGROUND OF THE INVENTION

High-frequency probes are required for the testing of fine layers as well as for the ultrasonic detection of minor faults. If the fault to be tested or the layer thickness to be checked becomes small compared to the wave length of the ultrasonic signals used, the non-homogeneity no longer represents an obstacle to the ultrasonic signal. The invention relates to probes having a frequency that is high enough to detect fine layers as well as minor faults. The probes typically have a frequency bigger than 20 MHz, the frequency generally ranges between 10 and 100 MHz, it may also be of 150 MHz and more.

The article of J. Büchler, M. Platte and H. Schmidt "Electronic circuit for high-frequency and broad band ultrasonic pulse-echo operation" in Ultrasonics, 1987, Vol 25, March, S. 1112 through 1114 discloses a probe with a transceiver transducer made of a thin PVDF-foil (polyvinylidenefluoride). Said foil is slowly charged by a transmitter electronics until a transmitting potential is attained and then, it is discharged as fast as possible. The discharge occurs by short-circuiting the transducer by means of an appropriate switch, which is embodied in the article by a transistor switch. The time of discharge is indicated as of 10 ns for a potential jump of 150 V, the capacity of the transducer designed as a foil is of 300 pF.

The ultrasonic pulse achieved is essentially unipolar and very short, his width is of approximately 50 ns.

The disadvantage of the probe of the art is that after an ultrasonic pulse has been sent out, a quite long period of waiting time elapses until it is ready for reception. The periods of idle time which have to be observed are not always acceptable for practical testing. Although it is on principle possible to work with a sufficiently long pre-located body and thus avoid the disadvantages of the periods of idle time that are to be observed, this has the disadvantage that, with the high-frequency pulses under discussion, the sound in the pre-located body is considerably attenuated. This disadvantage should be avoided.

The ultrasonic testing devices working according to the pulse-echo method usually are provided with a probe with a transceiver transducer as it is known out of the above-mentioned article. In principle, probes with separate transducers, that is with a transmitter transducer and a receiver transducer are also known. As an example, we are referring to the DE-book J. Krautkrämer and W. Krautkrämer "Materials Testing with Ultrasound" published by Springer, $6^{th}$ ed. In the probes with two transducers of the art the transducers are arranged side by side in the direction of sound propagation. Thus, the path followed by the ultrasound between the transmitter transducer and the receiver transducer is V-shaped. But this is detrimental to the testing of layers, since the measurement should occur perpendicularly to the boundary surfaces of the layers.

That is where the invention comes to bear. The object of the invention is to provide a probe that may be used in particular in the high-frequency range and that allows of the reduction of idle time and thus of a shorter design of the pre-located body while keeping possibly unchanged the advantages of the probe according to the article mentioned.

Starting with the probe of the type mentioned above, the solution of this object is to have the transmitter transducer and the receiver transducer made of the same material and to have the transmitter transducer and the receiver transducer arranged one behind the other in the direction of sound propagation and connected in a plane, in particular to have them glued one on top of the other.

This probe is provided—as actually known—with separate transducers for sending out and receiving the ultrasonic pulse. But now, the transducers are arranged directly one behind the other. Thus, the probe according to the invention essentially works like a probe with one transducer, since the two transducers are arranged one behind the other and are made of the same material.

When a transmitter transducer and a receiver transducer are arranged one behind the other in the direction of sound propagation, reflections occur between the two transducers. According to the invention, these reflections are avoided by connecting the two transducers in a plane, in particular by gluing them one on top of the other. Attention is particularly payed to the fact that the space between the two transducers is as small as possible. By using two transducers made of the same material, no reflections occur on the boundary surfaces.

The invention suggests therefore a spatial design of the two transducers being as similar as possible to the design of a probe with one transducer. The two transducers are electrically separated from each other though, so that a possible interference in the receiver electronics by the transmit pulse is largely excluded. Thus, the idle time is largely suppressed and is virtually no longer relevant. So far, it is possible to switch into receive position shortly after having sent out an ultrasonic pulse and, accordingly, the pre-travel to be used can be short. It is not always desirable to completely do without pre-travel, since the pre-travel also protects the transducers.

In a particularly preferred embodiment, the thickness of the glue layer between transmitter transducer and receiver transducer is as small as possible. It should be so small that there are virtually no reflections. The material preferably used for the glue layer is a material that has as far as possible the same sound characteristics as the material of which the transducers are made.

SUMMARY OF THE INVENTION

It proved to be particularly preferable to have the transmitter transducer and the receiver transducer built according to the same design principle. Particularly the sound fields of these two transducers should be as identical as possible. In this way, a probe with one transducer is being approximated as far as possible.

It proved to be advantageous to connect the transmitter transducer with an attenuator by its surface opposite the receiver transducer. Although such attenuators are well known in the art, it is advantageous for the present invention to have the transmitter transducer connected with the attenuator. The shortest possible pulses are thus obtained.

It likewise proved advantageous to connect the pre-located body with the receiver transducer. Although the receiver transducer is, in this arrangement, directly penetrated by radiation and although it accordingly yields an electrical signal to its electrode, this operation is very short and does virtually not affect measurement.

It proved particularly preferable to level the potentials of the adjacent electrodes of the two transducers, particularly to put them on mass potential. In this way, there are no problems of an electric separation between the two neighboring electrodes.

It is also advantageous to have the transmitter electronics and the receiver electronics arranged as near as possible to their respective transducer, particularly to have them accommodated in the same housing. Thus, interference due to parasitic capacitances and inductances is largely excluded.

In a particularly preferred embodiment, the transmitter electronics ends in low impedance, whereas the entry of the receiver electronics is highly resistive. The low impedance transmitter output permits the desired potential drops which should be as short as possible. Thanks to the highly resistive transmitter input, the receiver foil is charged as little as possible.

BRIEF DESCRIPTION OF THE DRAWINGS

Further advantages and characteristics of the invention will become clear in the remaining claims and in the following description of two embodiments that are only examples and are not limiting the scope of the invention, whereby said embodiments are explained in more detail with reference to the drawing. This drawing shows in:

DETAILED DESCRIPTION OF EMBODIMENTS OF THE INVENTION

Figure 1:
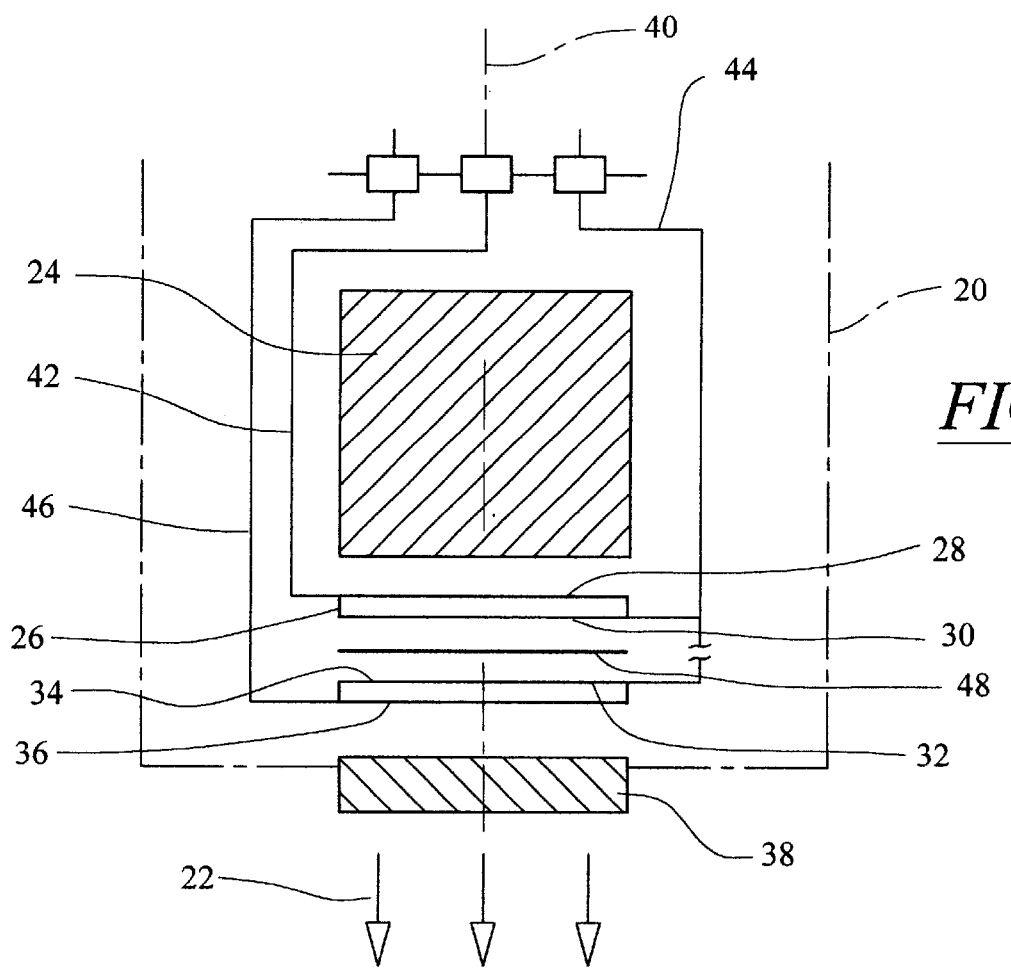
FIG. 1: an exploded side view of a probe.

In an only hinted at probe housing 20 an attenuator 24, a transmitter transducer 26 with an upper electrode 28 and with a lower electrode 30, a receiver transducer 32 with an upper electrode 34 and with a lower electrode 36 as well as a pre-located body 38 are arranged one behind the other in direction of propagation 22 (arrows) of the ultrasound. All these parts are round or cylindrical, they are accommodated in an equiaxed arrangement relative to an axis 40.

The attenuator 24 is made of a material that has possibly the same characteristic wave impedance as the two identical transducers 26, 32. It is in fact made of cast resin and is directly cast onto the transmitter transducer 26, that is onto its upper electrode 28. In axial direction, it has a length of approximately 10 mm.

The transducers used for the transmitter transducer 26 and for the receiver transducer 32 are identical in structure. On the basis of a finished PVDF-foil as it may be procured commercially the electrodes 28 and 30 and 34 and 36 respectively are applied by cathodic evaporation and then the electrodes are contacted. The corresponding junction lines 42, 44, 46 are shown in FIG. 1. Three soldering terminals are provided above the attenuator 24. The junction lines 42 through 46 are led to them.

The two transducers 26, 32 are connected together by a layer of glue 48. Said layer is located between the lower electrode 30 of the transmitter transducer 26 and the upper electrode 34 of the receiver transducer 32. It is as thin as possible. It can be made of a conductive material. Its thickness is selected in such a manner so that it is considerably smaller than the wave length for which the two transducers 26, 32 are designed.

In order to protect the sensitive foils, a pre-located body 38 made of polystyrene is arranged on the front side. Of all the materials tested, polystyrene has the least losses up to high frequencies of for example 100 MHz. It has a good impedance match with PVDF. A pre-located body made of acrylic glass is also possible, it has slightly higher losses. In one embodiment, this pre-located body 38 has a thickness of only a few millimeters (i.e. less than ten millimeters), typically has a thickness of between approximately 1 and 4 millimeters, and preferably has a thickness of approximately 2 millimeters.

The arrangement of the two foils of the transmitter transducer 26 and of the receiver transducer 32 is selected in such a manner so that a maximum of sensitivity is achieved. By using the rear foil as a transmitter transducer 26, this foil can better be attenuated. Thus, undesired reflections can be minimized at the rear side. The junction of the different materials has to be done very accurately, particularly air locks have to be avoided. In the frequency range even thinner junction layers, such as for example layers of glue, become noticeable.

Figure 2:
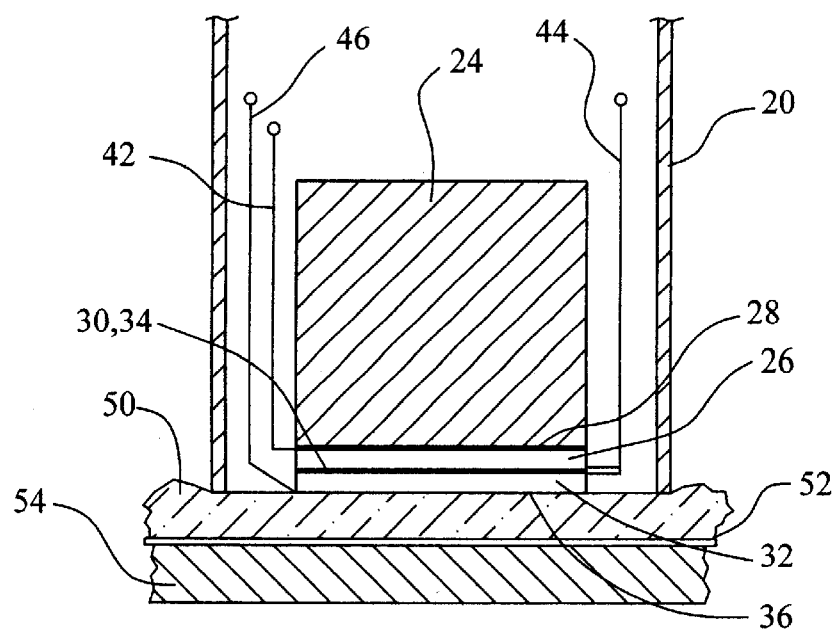
FIG. 2: a side view of a probe in a modified embodiment.

FIG. 2 shows another embodiment of the actual probe. In this case, the transducers 26, 32 are not made of prefabricate foils, here they are obtained through the application of the material PVDF by cathodic evaporation. This application by cathodic evaporation is either made on a very thin earth electrode 30, 34, which is provided for the two transducers 26, 32 together. An extremely thin gold foil or a foil of appropriate material is used. It is vaporized on both sides with PVDF in the same way. Then, the upper electrode 28 and the lower electrode 36 respectively are applied. Again, the attenuator 24 is cast onto the upper electrode 28. A pre-located body 38 made of a solid material is not provided this time. A water pre-travel 50 is used instead. FIG. 2 shows a thin layer 52 as it has to be tested by means of the probe, it is located on a support 54.

Figure 3:
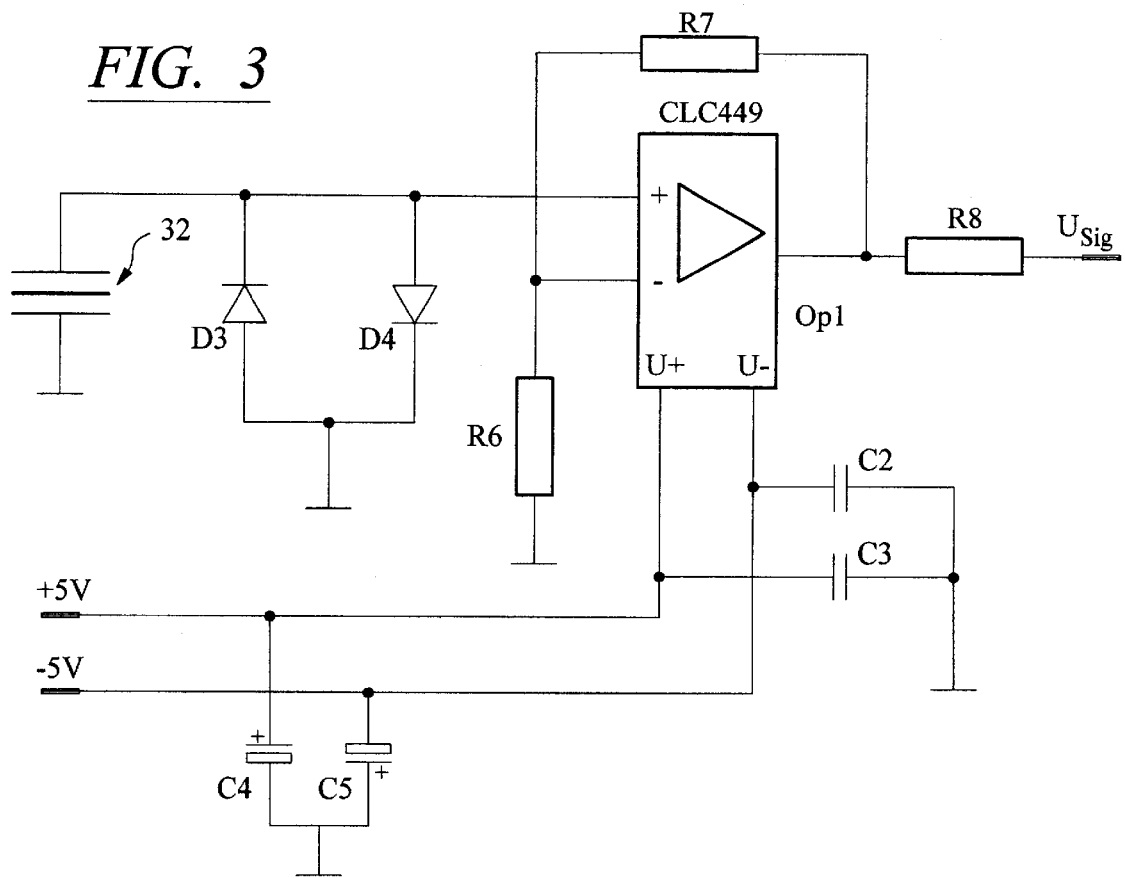
FIG. 3: an electronic connection diagram of the receiver electronics.

The transmitter transducer 26 is slowly charged by means of the transmitter electronics (FIG. 3), with a transmitting trigger pulse (SAP) it is discharged all of a sudden. Knowing the capacity C of the foil, the time constant of the time of charge may be adjusted via the resistor R1. The slow charging permits to prevent an acoustic signal from being radiated during charging.

The discharge of the transmitter transducer 26 occurs via the transistor V2. The transistor used here is a VMOS-transistor. This transistor is triggered, taking advantage of the avalanche effect in the transistor V1. The transmitter electronics is located inside the probe housing 20.

Figure 4:
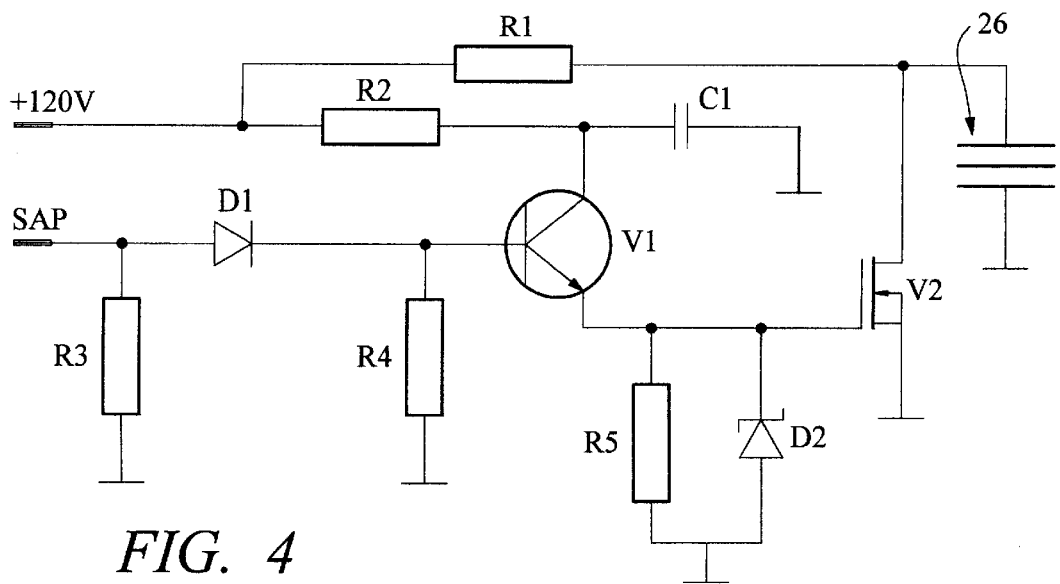
FIG. 4: an electronic connection diagram of the transmitter electronics.

The receiver electronics according to FIG. 4 is also integrated in the probe. Attention is payed to feed lines that should be as short as possible, they should be shorter than 2 cm, preferably even shorter. The receiver electronics utilizes an operational amplifier Opl of the type CLC 449 of the enterprise Comlinear, it is adjusted to quadruple amplification. It constitutes a highly resistive terminal of the receiver, in order not to load the receiving foil. A falsification of signals is thus avoided. The amplification is determined by the resistors R6 and R7. Finally, the operational amplifier is a cable driver for the following 50 ohms coaxial cable used for the signal transmission of the output signal Using.

Due to the conditions of mass prevailing on the common surface of the two transducers 26, 32, which are not ideal, an electrical disturbance of the transmitting signal occurs at the receiver transducer 32. The antiparallel connected diodes D3 and D4 are intended to limit this disturbance. At the same time, they guard the operational amplifier from coming into the saturation range.

The transmitter electronics and the receiver electronics have been realized in SMD-technology in order to minimize the size. The whole electronics thus fits on a printed board the size of which being of 15 mm×32 mm.

What is claimed is:

1. A probe for ultrasonic testing according to the pulse-echo method, for generating a short, possibly unipolar, ultrasound pulse, said probe comprising:

a transmitter transducer and with a receiver transducer;

wherein the transmitter transducer and the receiver transducer are provided with electrodes;

wherein the transmitter transducer and the receiver transducer are made of the same material and are each made of a plastic foil; and wherein the transmitter transducer and the receiver transducer are arranged directly one behind the other in the direction of sound propagation.

2. The probe according to claim 1, wherein the transmitter transducer and the receiver transducer have substantially identical sound fields.

3. The probe according to claim 1, wherein the transmitter transducer is connected with an attenuator by its surface opposite the receiver transducer.

4. The probe according to claim 1, wherein the receiver transducer is connected with a pre-located body by a surface opposite the transmitter transducer, and wherein the pre-located body has a thickness of less than approximately ten millimeters.

5. The probe according to claim 1, having the transmitter transducer connected with a transmitter electronics and the receiver transducer connected with a receiver electronics, wherein two directly adjacent electrodes are equipotential.

6. The probe according to claim 5, further comprising a probe housing, wherein the transmitter electronics and the receiver electronics are located proximate to the transducers.

7. The probe according to claim 5, wherein the transmitter transducer is connected to a low impedance output of the transmitter electronics and the receiver transducer is connected to a highly resistive receiver input.

8. The probe according to claim 1, wherein the transducers are made of PVDF-foils.

9. The probe according to claim 6, further comprising a probe housing, wherein the transmitter electronics and the receiver electronics are located in the probe housing.

10. The probe according to claim 1, wherein the receiver transducer is connected with a pre-located body by its surface opposite the transmitter transducer, and wherein the pre-located body has a thickness of between approximately one and four millimeters.

11. The probe according to claim 1, wherein the receiver transducer is connected with a pre-located body by its surface opposite the transmitter transducer, and wherein the pre-located body has a thickness of approximately two millimeters.

12. A method for operating a probe for ultrasonic testing according to the pulse-echo method, for generating a short, possibly unipolar ultrasound pulse, the probe having a transmitter transducer and a receiver transducer, wherein the transmitter transducer and the receiver transducer are provided with electrodes, are made of the same material, and are each made of a plastic foil, wherein the transmitter transducer and the receiver transducer are arranged directly one behind the other in the direction of sound propagation, said method comprising the steps of:

in order to produce the exciting potential of the transmitter transducer, feeding a slowly increasing potential to the receiver transducer; and once a sufficient potential has been reached, short-circuiting the transmitter transducer in the shortest period of time possible.

13. A probe for ultrasonic testing according to the pulse-echo method, for generating a short, possibly unipolar, ultrasound pulse, said probe comprising:

a transmitter transducer and a receiver transducer;

wherein the transmitter transducer and the receiver transducer are provided with electrodes;

wherein the transmitter transducer and the receiver transducer are made of the same material and are each made of a plastic foil;

wherein a substance is used to adhere together the transmitter transducer and the receiver transducer; and wherein the transmitter transducer and the receiver transducer are arranged directly one behind the other in the direction of sound propagation.

14. A probe for ultrasonic testing according to the pulse-echo method, for generating a short, possibly unipolar, ultrasound pulse, said probe comprising:

a transmitter transducer and a receiver transducer;

wherein the transmitter transducer and the receiver transducer are provided with electrodes;

wherein the transmitter transducer and the receiver transducer are made of the same material and are each made of a plastic foil; and wherein the transmitter transducer and the receiver transducer are glued together, and arranged directly one behind the other in the direction of sound propagation.

15. The probe according to claim 14, wherein the thickness of the glue between the transmitter transducer and the receiver transducer is substantially smaller than the wavelength for which the two transducers are designed.

16. The probe according to claim 14, having the transmitter transducer connected with a transmitter electronics and the receiver transducer connected with a receiver electronics, wherein two directly adjacent electrodes joined by the layer of glue are equipotential.

* * * * *